(12) United States Patent
Malin

(10) Patent No.: US 9,506,941 B2
(45) Date of Patent: Nov. 29, 2016

(54) DEVICE FOR THE HANDLING OF PETRI DISHES

(71) Applicant: LICONIC AG, Mauren (LI)

(72) Inventor: Cosmas G. Malin, Mauren (LI)

(73) Assignee: LICONIC AG, Mauren (LI)

( * ) Notice: Subject to any disclaimer, the term of this patent is extended or adjusted under 35 U.S.C. 154(b) by 2 days.

(21) Appl. No.: 14/294,602

(22) Filed: Jun. 3, 2014

(65) Prior Publication Data

US 2014/0377038 A1   Dec. 25, 2014

(30) Foreign Application Priority Data

Jun. 4, 2013   (CH) ........................................ 1060/13

(51) Int. Cl.
| | |
|---|---|
| *G01N 35/10* | (2006.01) |
| *C12M 1/22* | (2006.01) |
| *C12M 1/00* | (2006.01) |
| *C12M 1/26* | (2006.01) |
| *B25J 11/00* | (2006.01) |
| *G01N 35/00* | (2006.01) |
| *G01N 35/04* | (2006.01) |

(52) U.S. Cl.
CPC ................ *G01N 35/10* (2013.01); *B25J 11/00* (2013.01); *C12M 23/10* (2013.01); *C12M 23/50* (2013.01); *C12M 33/00* (2013.01); *G01N 2035/00356* (2013.01); *G01N 2035/0429* (2013.01); *G01N 2035/0465* (2013.01)

(58) Field of Classification Search
CPC .............................. C12M 23/10; G01N 35/04
See application file for complete search history.

(56) References Cited

U.S. PATENT DOCUMENTS

| | | | |
|---|---|---|---|
| 3,844,896 A | | 10/1974 | Sharpe |
| 4,090,921 A | | 5/1978 | Sawamura et al. |
| 4,166,006 A | | 8/1979 | Hertl et al. |
| 4,287,301 A | | 9/1981 | Astle |
| 5,578,268 A | * | 11/1996 | Champseix ............. B01F 9/002 141/130 |
| 2003/0085368 A1 | | 5/2003 | Kesil et al. |
| 2005/0019904 A1 | * | 1/2005 | Zarur .................... B01F 9/0001 435/291.7 |
| 2006/0115889 A1 | | 6/2006 | Nakashima et al. |
| 2010/0173416 A1 | | 7/2010 | Gupta et al. |
| 2012/0251275 A1 | * | 10/2012 | Malin ................... C12M 23/10 414/225.01 |
| 2014/0030802 A1 | | 1/2014 | Eberle et al. |

FOREIGN PATENT DOCUMENTS

| | | |
|---|---|---|
| DE | 102010060634 | 5/2012 |
| EP | 1661980 | 5/2006 |
| EP | 2482079 | 8/2012 |

OTHER PUBLICATIONS

European Office Action in related application No. EP14001927 dated Nov. 20, 2014.

* cited by examiner

*Primary Examiner* — Jill Warden
*Assistant Examiner* — Matthew Krcha
(74) *Attorney, Agent, or Firm* — Greenblum & Bernstein, P.L.C.

(57) ABSTRACT

A rotating holder to invert Petri dishes by 180° and to loosen the bottom from the cover, which has two positions to accommodate Petri dishes. By inverting the rotating holder around a rotation axis, the Petri dishes are reversed and inverted in the two positions. Thus the bottom of the upper Petri dish will be lowered and be engaged by a gripper.

21 Claims, 3 Drawing Sheets

DEVICE FOR THE HANDLING OF PETRI DISHES

CROSS REFERENCE TO RELATED APPLICATION

This application claims priority from Swiss Patent Application No. 1060/13 filed on Jun. 4, 2013. The entire contents of the priority application are incorporated herein by reference.

FIELD OF THE INVENTION

The invention relates to a device for the handling of Petri dishes, a storage device having such a device for the handling of Petri dishes, and a method of operating the device

BACKGROUND

Petri dishes are flat, round, generally transparent dishes with a bottom and a cover that overlaps the bottom, which are widely used in biology, medicine, or chemistry. Thus, Petri dishes are used for the cultivation of microorganisms and cell cultures.

Microorganisms are introduced in situ into a nutrient medium in the bottom. Then the Petri dishes are usually incubated with the cover on the bottom and the nutrient medium on the top. In this storage, the weight of the plate rests upon the cover, wherein the seal between the cover and the dish is improved. Excess water is not formed on the nutrient medium, rather is accumulated on the cover.

During the incubation period, the growth of the cultures is frequently inspected visually. For applications in which large numbers of plates are worked with, there is a need for automation of this process. Thus, a Petri dish is removed from the incubator and/or the storage device according to a specific timetable, and a processing device, especially an analysis device, is introduced. For the inspection, the plates should be introduced into the inspection device with the culture medium down.

For transferring the Petri dishes between storage and the inspection device, a transfer device is needed. Usually this has a pivot arm that is arranged on a wall of the incubation chamber or storage device. A Petri dish is engaged by a vacuum suction device, which is arranged at the outer end of the pivot arm, and is simultaneously removed from the incubator and inverted by a 180 degree rotational movement. The vacuum suction component in the inspection device must be removed for the inspection.

A device is known from EP 2 482 079, in which only the bottom of the Petri dishes is inverted.

Other solutions are based on the Petri dishes being inverted by a transport lift within the incubator. Here there is a risk of contamination of the entire incubator due to the possibility of the loss of the plate.

DISCLOSURE OF THE INVENTION

The aim is to provide a device for the handling of Petri dishes, a storage device having such a device for the handling of Petri dishes, and a method of operating the device, which has high throughput This aim is solved by the independent claims. Accordingly, the device has a rotating holder that is rotatable around a particularly horizontal rotation axis. At least a first and a second holder for Petri dishes are arranged on the rotating holder, wherein the first holder is brought from a lower position to an upper position and the second holder is brought from the upper position to the lower position by rotating the rotating holder, and the Petri dishes being held in the holders can be inverted thereby. This design in which at least two Petri dishes are inverted simultaneously and are moved back and forth between two positions enables a process with high throughput.

The first and second holders are preferably arranged at 180° around the rotation axis.

Advantageously, each holder has a cover holder for receiving the cover of a Petri dish, and a pressure element wherein the pressure element and the cover holder can be moved radially with respect to one another. The terms "radial" and "radially" as used in the description and the claims are to be understood in respect to the rotation axis of the rotating holder, i.e., it describes an axis or direction that is perpendicular to the rotation axis and intersects the rotation axis.

In a particularly advantageous embodiment, the radial movement is generated by a spread drive, which is common to the two holders, and with which the pressure elements can be moved radially outwards, and thus can be moved against the covers of the Petri dishes held in the holders.

Further, each cover holder advantageously has a cover-holder device, with which the cover can be held in the upper position without the bottom. The cover holder device can have clamping elements, between which the cover can be securely clamped by lateral forces. The phrase "lateral forces" here is understood as forces that act on the side of the cover, i.e., that are directed against the lateral walls thereof from the outside.

The device may have a gripper with which the bottom of a Petri dish located in the upper position can be gripped and can be taken out of this position or be introduced into this position. This gripper can advantageously be moved in a direction that is translationally parallel to the direction of rotation of the rotating holder, and can have clamping members between which the bottom can be securely clamped through lateral forces. The phrase "lateral forces" in this case is understood as forces that act on the side of the bottom, i.e., that are directed against the lateral walls of the bottom from the outside.

The invention also relates to a storage device for storage and manipulation, e.g., inspection, of Petri dishes. The storage device has the above-mentioned device for the handling of Petri dishes and additionally has storage for receiving a plurality of Petri dishes with the cover downwards, and a processing device. The system is designed so that the Petri dishes can be inverted with said device for the handling of Petri dishes on their transport path between the storage and the processing device.

Finally, the invention also relates to a method for operating said apparatus comprising:

a) the first holder is brought to the lower position and the second holder is brought to the upper position;

b) a first Petri dish is positioned in the first holder and a second Petri dish is positioned in the second holder—this can take place before, during or after step a) takes place;

c) the first holder with the first Petri dish is brought to the upper position and the second holder with the second Petri dish is brought to the lower position by rotating the rotating holder around the rotation axis, while the cover and the bottom of each Petri dish are pressed together.

BRIEF DESCRIPTION OF THE FIGURES

Further embodiments, advantages and applications of the invention will become apparent from the dependent claims and from the following description with reference to the figures. Thus:

DETAILED DESCRIPTION OF EMBODIMENTS OF THE DISCLOSURE

Figure 1:
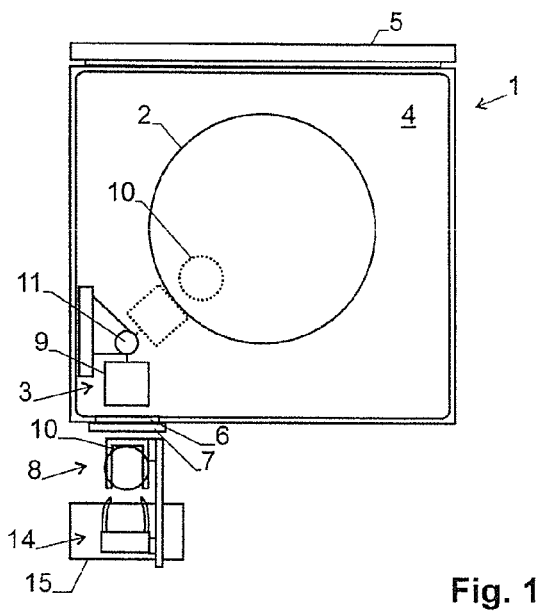
FIG. 1 shows a schematic top view of a storage device for Petri dishes.

FIG. 1 shows a storage device for Petri dishes. This comprises an incubator 1, having arranged therein a storage space 2 in the form of a carousel, and a transport device 3. Components of this type have been described, for example, in EP 2 482 079. In storage space 2 are arranged the Petri dishes 10, which respectively have a cover and a bottom, stored with the cover facing down, while the culture to be incubated is arranged on the upper-lying Petri dish bottom.

The incubator 1 is a climate chamber, in the interior space 4 of which a predetermined temperature, atmosphere and/or humidity can be maintained. On one side of the incubator 1 is arranged a user door 5 through which the user can access the interior space 4. On the side of the incubator 1 opposite the user door 5 there is an airlock opening 6, which can be closed with a motorized airlock door 7.

The transport device 3 serves to move the Petri dishes 10 through the airlock opening 6 between the storage space 2 and a rotating holder 8 arranged outside of the incubator 1. The rotary holder 8 will be described in detail below. The transport device 3 has a scoop 9 that can receive a respective Petri dish 10. The scoop 9 is vertically adjustable, pivotable around an axis 11, and radially extendable to the axis 11. The rotating holder 8 is arranged outside the airlock hole 6 such that a Petri dish 10 is introduced with the transport device by linear translational movement through the airlock hole 6 into a lower position (described below) of the rotating holder 8, or removed therefrom, advantageously by the linear translational movement that is generated by horizontally extending and retracting the scoop 9. The translational movement for loading the rotating holder 8 proceeds parallel to a rotation axis (likewise further described below) of the rotating holder 8.

Figure 2:
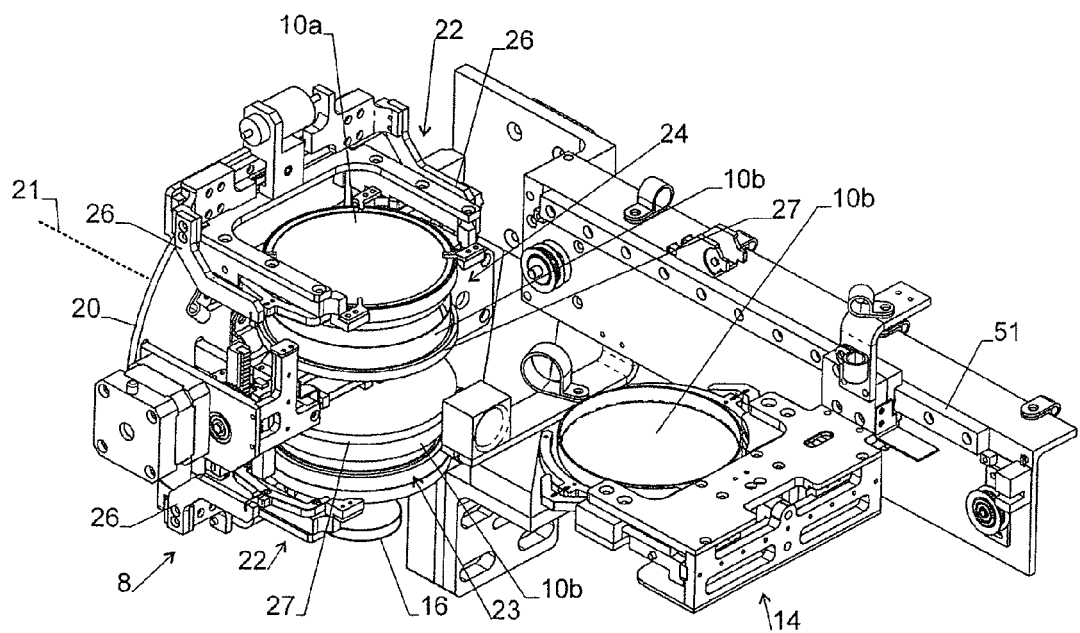
FIG. 2 shows a device for the handling of Petri dishes with a rotating holder and gripper.

The components of the system arranged outside of the incubator 1 are referred to in this text and in the claims as "device for the handling of Petri dishes". They comprise in particular the above-mentioned rotating holder 8, a gripper 14, an analysis device 15 (or, formulated more generally, a processing device), and inspection camera 16 (FIG. 2). These components, which are described in more detail below, fulfill the following roles:

The rotating holder 8 serves to invert the Petri dishes coming from storage space 2 (or returning there) so that the bottoms come to face down, and to separate the bottom and the cover so that the bottom can be gripped by the gripper 14.

The gripper 14 serves to bring the bottom of a Petri dish to the analysis device 15, where the culture is, for example, analyzed visually.

The inspection camera 16 serves to check the Petri dish for contamination with dangerous bacteria before separating the cover and bottom, so that the opening of the Petri dish can be disabled in the event of contamination, and the escape of undesired germs can be avoided.

The analysis device 15 inspects the bottom of the Petri dish in the opened state.

A possible configuration of the rotating holder 8 can be developed from the FIGS. 2 through 6. It has a rotating body 20 that can be rotated at least 180° by a drive around a horizontally running rotation axis 21. On rotating body 20 are arranged two holders 22 (FIGS. 2, 3), which can respectively receive a Petri dish. The holders 22 can be rotated by rotating the rotating body 20 around the rotation axis 21 in such a way that in each case one thereof is located in a lower position 23 and the other in an upper position 24.

Figure 3:
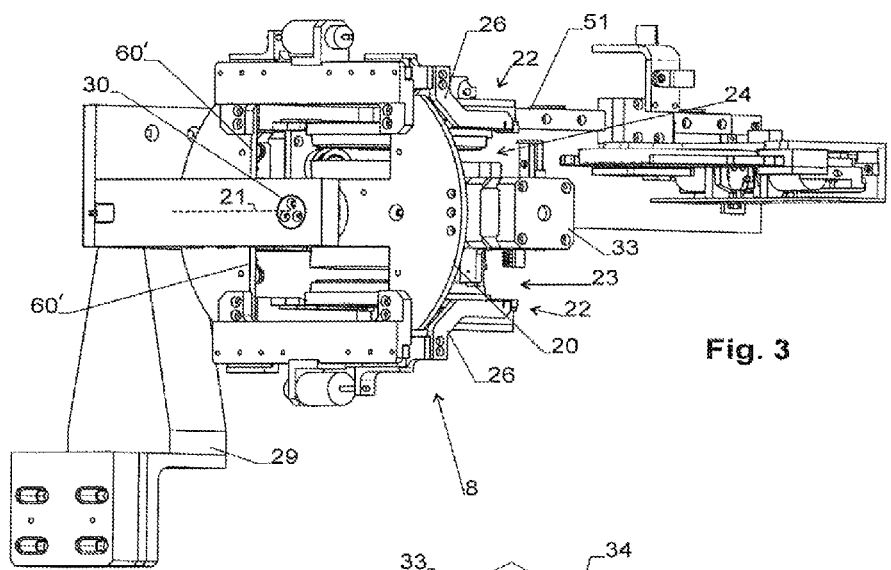
FIG. 3 shows a cross-sectional view of the device according to FIG. 2.

As can be seen from FIG. 3, a holder 29 is provided, which can be attached to the outside wall of the incubator 1, and carries the rotating holder 8 in an opening 30 rotatably around the rotation axis 21.

Each holder 22 has a cover holder 26 for receiving and retaining the cover 10a of a Petri dish, and a pressure element 27 with which the bottom 10b can be pressed against the cover 10a. For this purpose, the cover holder 26 and the pressure element 27 can be moved radially with respect to one another. In the embodiment shown for this purpose, the two pressure elements 27 are radially moveable while the cover holder 26 is in a fixed radial position.

A common spread drive is provided to move the pressure elements 27. This comprises a spread motor 33 arranged on the rotating body 20. The drive pinion of the spread motor 33 drives two racks 34 (FIG. 4, 5) which move in opposite directions in a direction perpendicular to the rotation axis 21. A first spring retainer 35 is arranged on each rack 34, and each spring retainer 35 holds two parallel leaf springs 36. These leaf springs, which are connected via the first spring retainer 35 and the rack 34 with the spread drive, extend perpendicular to the rotation axis 21. They are arranged so that their surface normals (i.e., the surface normals of each of the two largest surfaces of each leaf spring) are perpendicular to the rotation axis 21. The leaf springs 36 lying on the opposite ends of the first spring retainer 35 are each attached to a second spring retainer 39, each one of which in turn carries one of the pressure elements 27. Each of the two leaf springs 36 associated with a pressure element 27 has a different distance to the rotation axis 21. In this manner, a resilient storage space is available for each pressure element, which allows a radial displacement of the pressure elements but prevents tilting of the pressure elements.

Each pressure element 27 is formed from a plate that has a raised circular rim 41 which guides the bottom 10b of the Petri dish laterally into the upper position 24.

Figure 6:
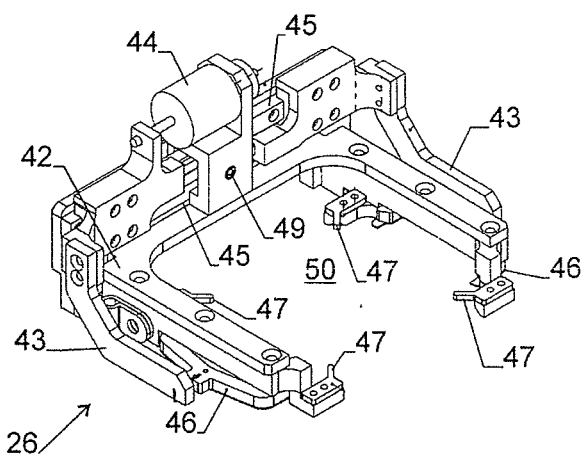
FIG. 6 shows an embodiment of the cover holder.

As can be seen in particular from FIG. 6, each cover holder 26 has a frame 42 that is securely connected to the rotating holder 8. The frame 42 includes two mutually movable arms 43 that are slidably mounted, which can be synchronously moved relative to one another by a drive 44. To ensure a synchronized movement of the arms 43, racks 45 are arranged on the arms 43 to engage on opposite sides of a pinion (see pinion storage space 49). The drive 44 is designed as a linear drive, with which the arms 43 can be pressed apart against a spring force.

On each arm 43 is resiliently mounted a finger 46 that carries two counter-bearings 47, which are positioned such that the cover 10*a* of a Petri dish arranged in the holder is supported radially from the outside. That is, the two counter-bearings 47 radially support, from an outside, the cover 10*a* of the Petri dish arranged in the holder.

To hold the cover of a Petri dish securely, the arms 43 are moved toward each other so that the tips of the fingers 46 press against the outside of the cover and clamp it securely.

The components of the cover holder 26 shown in FIG. 6 are arranged around an open area 50, through which at least 80%, especially at least 90%, of the cover of the Petri dish is observable radially from the outside. In this way, a visual inspection by the aforementioned inspection camera 16 is possible when a Petri dish is in the down position 23. The inspection camera 16 receives an image of the incubate radially from the outside through the cover 10*a* to inspect same, and to detect, for example, any unexpected growth by foreign bacteria.

To improve the contrast for the inspection camera 16, each of the plate-shaped pressure elements 27 on the respective facing side of the Petri dish (Petri dish side) is optically homogeneous, i.e., the reflectivity varies across the surface by a maximum of 10%. In particular, the Petri dish side surface is dark, i.e., it has an optical reflectivity of less than 20%, in particular less than 10%, for at least one wavelength between 300 and 1000 nm. The wavelength mentioned is the wavelength (or the wavelength range) at which the measurement results are carried out by the inspection camera 16.

As can be seen from FIGS. 2 and 3, a linear guide 51 is arranged on the holder 29, on which the gripper 14 can be moved in a direction parallel to the rotation axis 21.

Figure 7:
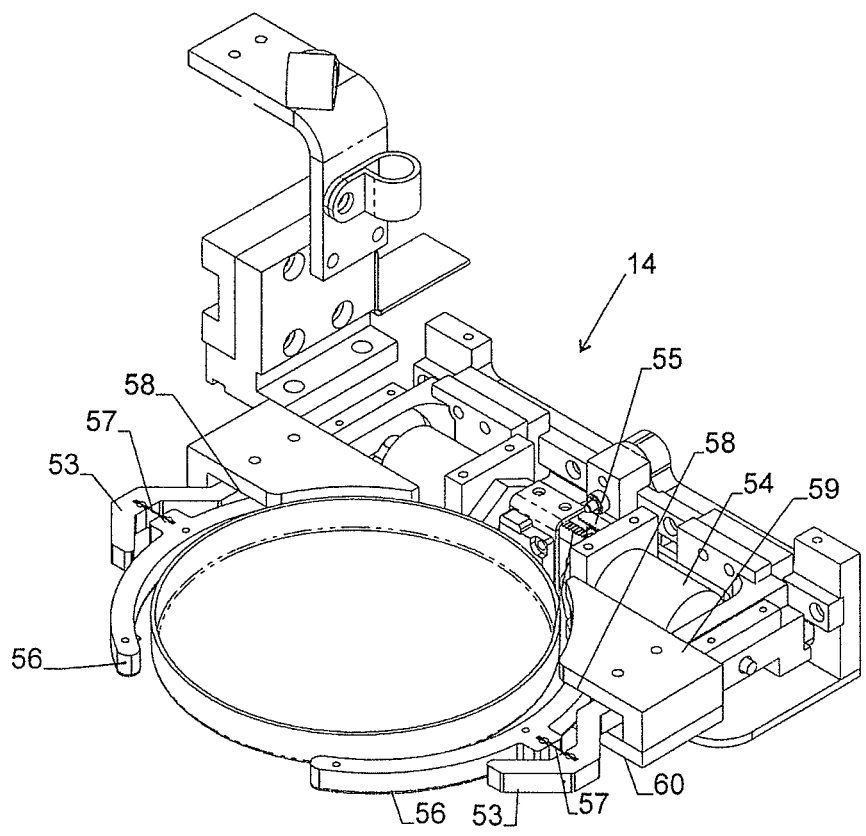
FIG. 7 shows an embodiment of a gripper.

The configuration of the gripper 14 is given in FIG. 7. The gripper has clamping members to clamp the bottom 10*b* of the Petri dish securely in the upper position 24 by lateral forces. Similarly to the cover holder 26, the clamping members are held on a pair of arms 53, which can be moved synchronously relative to one another by a drive 54. To synchronize the movement of the arms 53, they are attached to racks 55 that engage the opposing sides of a pinion.

The gripping members of the gripper 14 have fingers 56, which are held resiliently on the leaf springs 57. Each finger engages with its guide 58 at the opposite end from the rotating holder 8. This guide is formed by the gap between two plates 59, 60 that are spaced apart, and limits the upward and downward movement of the member, and thus of the fingers 56, so as to avoid damage.

The gripper 14 is arranged so that it can engage the bottom 10*b* of a Petri dish in the upper position 24 and/or and scan store it in the upper position 24.

The rotating holder 8 has recesses 60' (FIG. 3) on the oppositely lying sides from the gripper 14 through which the transport device 3 of the system can access each Petri dish in the lower position 22.

The operation of the described system is as follows:

If a Petri dish 10 is to be removed from the storage space 2 and brought to the analysis device 15, the storage space 2 is rotated so that the transport device 3 can access the desired Petri dish 10. The transport device 3 uses the scoop 9 to remove the Petri dish 10 from the storage space 2. The airlock door 7 is opened and the scoop 9 is moved in a linear translational motion through the airlock opening 6. It places the Petri dish in the cover holder 26 of the holder 22 in the bottom position 23. The side of the cover 10*a* is fixed by the clamping device of the cover holder 26. The pressure elements 27 are spread apart so that the lower pressure element presses against the bottom 10*b* of the Petri dish stored in the lower position 23 so that the bottom 10*b* is fixed to the cover 10*a*.

At the same time, the inspection camera 16 can be used to inspect the Petri dish before or afterwards for foreign germs. If a foreign germ is recognized, then, for example, the alarm is sounded and the Petri dish can be discarded.

Then, the rotating holder 8 is rotated 180° around the rotation axis 21. In this way, the Petri dish is inverted so that after the rotation of the rotating holder 8, in the upper position 24 the cover 10*a* will be on top and the bottom 10*b* will be on the bottom. Simultaneously, a second Petri dish that has possibly previously been in the upper position is moved downward and reinverted back.

Then, the spread drive 33 is put into operation, and the pressure elements 27 are moved from their extended position to an intermediate position. In this way, the bottom 10*b* of the Petri dish is lowered into the upper position 24 and is disengaged from the cover. At the same time, a second Petri dish is released in the lower position 23 so that, for example, it can be engaged by the transport device 3 and transferred to the storage space 2.

Then, the gripper 14 with its fingers 56 moves into the upper position 24, and there engages the bottom 10*b* of the Petri dish. Thereafter, the spread drive 33 is again activated to bring the pressure members 27 from their intermediate position to a radially innermost position. Thus, the rim 41 of the upper pressure member 27 is lowered below the bottom 10*b* so that the gripper 14 can bring the bottom 10*b* out from the upper position and move it to the analysis device 15 without colliding with the edge 41.

The gripper 14 then brings the bottom 10*b* to the analyzer 15 where the incubate can be analyzed.

To bring the bottom 10*b* and the Petri dish back to the storage space 2, the bottom 10*b* is first brought back to the upper position 24 by the gripper 14, the pressure elements 27 are extended to the radially outermost position, the rotating holder 8 is rotated and the transport device 3 removes the Petri dish from the lower position 22 for return to the storage space 2.

In the embodiment described, ball chain bearings are advantageously used with the linear guides.

Figure 4:
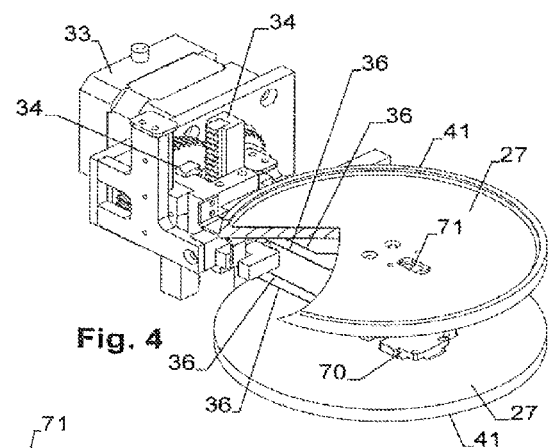
FIG. 4 shows an embodiment of the pressure elements with spread drive.
Figure 5:
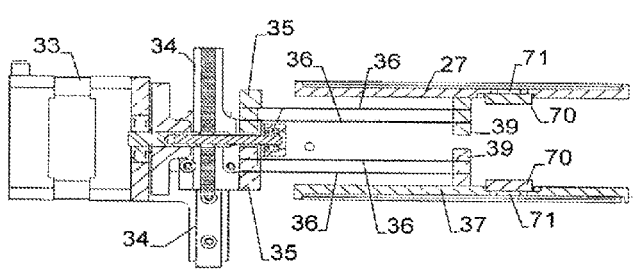
FIG. 5 shows the arrangement of FIG. 4 seen from the side.

For detecting the presence of Petri dishes in the holders 22 and/or in the gripper 14, suitable sensors can be used such as, for example, optical sensors. An example of such a sensor 70 for the holders 22 is shown in FIGS. 4 and 5. It is mounted at the pressure member 27 and configured to carry out optical reflection measurements at the Petri dish bottom 10*a* through an opening 71.

In the above embodiments, the claimed device for the handling of Petri dishes is arranged outside of the incubator 1. Basically, however, it could also be arranged within the incubator 1.

The pressure elements 27 are freely positionable and their various positions can be adjusted according to the respective requirements. In particular, the radially outermost position can be adapted to the height of the load, i.e., to the height of the Petri dish. In addition, the positions of the pressure elements can be adjusted to the swivel height and entry height of the gripper.

In the above embodiments, the rotating holder 8 has two holders 22 for Petri dishes. Also conceivable are embodiments that have more than two holders, e.g., three or four holders, which are distributed uniformly over the circumference of the rotating holder 8. In this case, the rotating holder 8 would rotate less than 180° in each operational step.

In this case, the pressure elements 27 would be configured so that only the Petri dishes in the uppermost and lowermost positions could be released.

As mentioned, the arms 43, 53 are advantageously moved synchronously with respect to one another, which is realized in the above-described embodiments with racks that engage on opposite sides of a pinion. Alternatively, other mechanical (or electrical) devices for synchronizing the arm positions can also be used, such as cams or joints.

While the preferred embodiments of the invention are described in the present application, it is clearly understood that the invention is not limited thereto, and may be embodied in other ways within the scope set out in the following claims.

The invention claimed is:

1. Device for the handling of Petri dishes that have a bottom and a cover, wherein the device is implemented so as to receive a Petri dish with underlying cover and at least inverting and delivering the bottom of the Petri dish, or vice versa, wherein the device comprises:
   a rotating holder having a rotatable body that is rotatable around a rotation axis;
   at least a first holder and second holder for respective Petri dishes arranged on the rotatable body; and
   a drive structured and arranged to rotate the rotatable body,
   wherein by rotating the rotatable body by approximately 180° the first holder can be brought from a lower position to an upper position and the second holder can be brought from the upper position to the lower position such that the respective Petri dishes held in the holders are invertable,
   wherein each of the first and second holder comprises:
   a cover holder structured and arranged for receiving the cover of a Petri dish, and a pressure element,
   wherein the pressure element and the cover holder are movable relative to one another radially with respect to the rotation axis so that the cover of the Petri dish can be pressed against the bottom of the Petri dish, and
   the device further comprising a common spread drive, wherein the pressure elements of both holders are movable radially outward by the common spread drive.

2. Device according to claim 1, wherein each pressure element is coupled with the spread drive via at least two parallel leaf springs, wherein the surface normals of the leaf springs are perpendicular to the rotation axis and the leaf springs are at different distances from the rotation axis, such that the leaf springs permit a resilient radial displacement without tilting the pressure elements.

3. Device according to claim 1, wherein the pressure elements are formed from optically homogeneous plates on the Petri dish side.

4. Device according to claim 3, wherein the plates have an optical reflectivity of less than 20% at least at a wavelength between 300 and 1000 nm.

5. Device according to claim 1, wherein the cover holder has an open area through which at least 80% of the Petri dish cover is radially observable from the outside.

6. Device according to claim 5, wherein the cover holder comprises counter-bearings, wherein the counter-bearings are positioned so that the counter bearings radially support, from an outside, the cover of a Petri dish arranged in the holder.

7. Device according to claim 5, wherein at least 90% of the Petri dish cover is radially observable from the outside.

8. Device according to claim 1, wherein each cover holder comprises a cover holding device with which the cover can be held securely in the upper position without the bottom.

9. Device according to claim 8, wherein the clamping members are held on two arms, wherein the arms are synchronously movable with respect to one another by a drive.

10. Device according to claim 9, further comprising gear racks that engage facing sides of a pinion, wherein the two arms are arranged on the gear racks that engage the facing sides of the pinion.

11. Device according to claim 8, wherein the cover holding device comprises clamping members between which the cover can be clamped securely through lateral forces.

12. Device according to claim 1, further comprising an inspection camera with which a Petri dish located in the lower position can be inspected radially through the cover from the outside.

13. Device according to claim 1, further comprising a gripper with which the bottom of a Petri dish can be withdrawn from the upper position or introduced into the upper position.

14. Device according to claim 13, wherein the rotating holder has open areas on one of the sides facing the gripper through which Petri dishes can be introduced into and/or withdrawn from the lower position.

15. Device according to claim 1, wherein the first holder and the second holder for respective Petri dishes are fastened to the rotatable body.

16. A system comprising a storage device for the storage and manipulation of Petri dishes in combination with and the device for the handling of Petri dishes according to claim 1, the storage device comprising a storage space to accommodate a plurality of Petri dishes with the cover downwards and a processing device, wherein the Petri dishes can be inverted onto a transport path between the storage space and the processing device by the device for the handling of Petri dishes.

17. System according to claim 16, wherein the storage space is arranged in an incubator having an air-lock opening, and further comprising a transport device arranged in the incubator, and structured and arranged for moving Petri dishes between the storage space and the rotating holder through the air-lock opening, wherein the rotating holder is arranged outside the air-lock opening so that a Petri dish can be introduced into or removed from the lower position via linear translational movement through the air-lock opening by the transport device.

18. System according to claim 17, wherein the linear translational movement is parallel to the rotation axis.

19. Method for operating the device for the handling of Petri dishes according to claim 1 comprising:
   a) bringing the first holder to the lower position and bringing the second holder to the upper position,
   b) positioning a first Petri dish in the first holder and positioning a second Petri dish in the second holder, either before, during or after step a),
   c) bringing the first holder with the first Petri dish to the upper position and bringing the second holder with the second Petri dish to the lower position by rotating the rotating holder around the rotation axis, while the cover and the bottom of each Petri dish are pressed together.

20. Device for the handling of Petri dishes that have a bottom and a cover, wherein the device is implemented so as to receive a Petri dish with underlying cover and at least inverting and delivering the bottom of the Petri dish, or vice versa, wherein the device comprises:
- a rotating holder having a rotatable body that is rotatable around a rotation axis;
- at least a first holder and second holder for respective Petri dishes arranged on the rotatable body; and
- a drive structured and arranged to rotate the rotatable body,
- wherein by rotating the rotatable body by approximately 180° the first holder can be brought from a lower position to an upper position and the second holder can be brought from the upper position to the lower position such that the respective Petri dishes held in the holders are invertable,
- the device further comprising a gripper with which the bottom of a Petri dish can be withdrawn from the upper position or introduced into the upper position,
- wherein the gripper is translationally movable in a direction parallel to the rotation axis and comprises clamping elements between which the bottom can be clamped securely through lateral forces.

21. Device according to claim 20, wherein the clamping elements comprise fingers structured and arranged for pressing against the bottom, wherein the fingers are held resiliently and engage a guide on their ends opposite to the rotating holder, wherein the guide limits upward and downward movement of these ends of the fingers.

* * * * *